United States Patent [19]

Solomon

[11] 4,255,341
[45] Mar. 10, 1981

[54] CATALYST AND PROCESS FOR PRODUCING ETHYLENE OXIDE

[75] Inventor: Paul W. Solomon, Bartlesville, Okla.

[73] Assignee: Phillips Petroleum Company, Bartlesville, Okla.

[21] Appl. No.: 22,919

[22] Filed: Mar. 22, 1979

[51] Int. Cl.³ ............... C07D 301/10; B01J 21/04; B01J 23/02; B01J 23/50
[52] U.S. Cl. ............... 260/348.34; 252/463; 252/475; 252/476
[58] Field of Search ............ 252/463, 476, 475; 260/348.34

[56] References Cited

U.S. PATENT DOCUMENTS

| | | | |
|---|---|---|---|
| 2,593,100 | 4/1952 | Calingaert | 252/463 |
| 2,773,844 | 12/1956 | Carlson et al. | 252/463 |
| 2,805,207 | 9/1957 | Metzger | 252/476 |
| 2,831,870 | 4/1958 | McClements et al. | 260/348.5 |
| 3,305,492 | 2/1967 | Ameen | 252/463 |
| 3,461,140 | 8/1969 | Titzenthaler | 260/348.5 |
| 3,794,588 | 2/1974 | Stiles | 252/462 |
| 3,887,491 | 6/1975 | Ramirez et al. | 252/476 X |

*Primary Examiner*—W. J. Shine

[57] ABSTRACT

A supported silver-containing catalyst suitable for the oxidation of ethylene to ethylene oxide is prepared directly from silver nitrate. The oxidation of ethylene using that catalyst is also disclosed.

17 Claims, No Drawings

CATALYST AND PROCESS FOR PRODUCING ETHYLENE OXIDE

This invention relates to the oxidation of ethylene to ethylene oxide with a silver-containing catalyst. In another aspect this invention relates to a novel method of producing a catalyst that is effective for catalyzing the oxidation of ethylene to ethylene oxide.

It is known that ethylene oxide can be prepared by reacting ethylene with oxygen at elevated temperatures in contact with silver catalysts. The catalysts may consist solely of silver, but generally supported catalysts are employed. The active catalyst layer may be applied to the support in several different ways. For example, it is possible to dip the carrier into a melt of silver, to coat it with a layer of silver oxide which is then reduced, or to deposit the silver electrolytically. The most commonly used technique of preparing a supported silver oxidation catalyst has involved preparing silver oxide by treating an aqueous solution of silver nitrate with an alkali metal hydroxide; recovering the silver oxide; depositing the silver oxide on the support; and activating the catalyst by reduction or calcination.

An object of the present invention is to provide a more simple method of preparing a supported silver catalyst for the oxidation of ethylene to ethylene oxide.

Another object of the present invention is to provide an improved process for oxidizing ethylene to ethylene oxide wherein the selectivity to ethylene at certain conversion levels is greater than obtained with catalyst prepared by prior art methods.

Other objects and advantages will be apparent from the following description.

In accordance with the present invention a process of preparing a catalyst is provided consisting essentially of combining aqueous silver nitrate with a suitable solid support in an amount which will result in said catalyst containing about 2 to about 75 weight percent silver based on the weight of said solid support, then drying the thus treated support at a temperature in the range of about 100° C. to about 200° C. to remove substantially all the water associated with said support, and then calcining the dried support at a temperature in the range of about 250° C. to about 800° C. to obtain an active catalyst.

Further, in accordance with the present invention there is provided a process for producing ethylene oxide employing a catalyst prepared as described in the preceding paragraph.

Supports, or supporting materials, employed in the production of supported silver catalysts in accordance with the invention comprise any of the solid supports heretofore employed in catalyst preparation. The support material may be completely inert or it may be one having a promoting or synergistic effect upon the finely divided metallic silver. Suitable supports comprise, for example: naturally occurring materials such as clays, bauxite, dawsonite, Florida earth, bentonite, kaolin, montmorillonite, green sand, the zeolites, diatomaceous earth, kieselguhr, infusorial earth, etc.; treated clay and clay-like materials; artifically prepared materials, such as permutites, activated alumina, silica gel, synthetic zeolites, charcoal, and the like; highly porous substances such as aluminum oxide, refractory Alundum, tabular corundum, silicon carbide, silica, crushed brick, magnesia, etc. Of the available catalyst support materials those consisting essentially of a porous structure are preferred. Catalysts possessing particularly desired characteristics are obtained by the use as the support of materials possessing adsorbent properties. The support material may be subjected to any conventional pretreatments directed to its activation, stabilization or to improving its characteristics.

An especially preferred support is alpha-alumina. The present process of producing support silver catalysts has been found to produce very active catalysts particularly with alpha-aluminas having low surface area, i.e., those having a surface area of less than 1.0 $m^2/g$.

The aqueous silver nitrate is applied to the support in an amount which will result in a catalyst containing about 2 to about 75 weight percent silver based on the weight of the support. In preferred embodiments the aqueous silver nitrate is employed in an amount which results in a catalyst containing about 10 to about 50 weight percent silver based on the weight of said solid support. An especially preferred embodiment involves employing silver nitrate in an amount which will result in a catalyst containing about 30 weight percent silver based on the weight of said solid support.

The drying of the thus treated support is carried out at a temperature no greater than about 200° C. The drying is continued until substantially all the water associated with the support has been removed. The time required to achieve such a result can be readily determined by routine gravimetric analysis. Generally the drying is carried out for about 1 to about 20 hours.

The calcination is carried out at a temperature in the range of about 250° C. to about 800° C., preferably about 500° C. to 700° C., the latter temperature range being especially preferred when the silver nitrate is used in an amount such that the catalyst will contain about 30 weight percent silver based on the weight of the solid support. Calcination can be carried out within a tubular reactor of the type conventionally used in the catalytic oxidation of ethylene to ethylene oxide. Alternatively the calcination can be conducted in an outside calcination zone. Preferably the calcination is conducted in the presence of an insert or an oxidizing atmosphere. Use of an inert atmosphere will generally require longer heating times. The calcination is continued until one obtains a catalyst active for the oxidation of ethylene to ethylene oxide. Generally about an hour under calcination conditions is sufficient to yield an active catalyst in accordance with this invention.

The catalyst prepared in accordance with this invention, as described above, can be used in the direct oxidation of ethylene to produce ethylene oxide. In the oxidation process the ethylene is contacted with an oxygen-containing gas in the presence of the inventive catalyst in a reaction zone at a temperature in the range of about 150° C. to about 500° C., preferably about 250° C. to about 400° C. The oxidation process can be carried out at atmospheric, subatmospheric, or superatmospheric pressure up to, for example about 500 psig. Generally it is preferred to conduct the oxidation at pressures from about atmospheric to about 300 psig.

Ethylene to be oxidized with the aid of the catalysts of the invention need not necessarily be essentially pure ethylene and may comprise normally gaseous diluents which have no substantial adverse effect upon catalyst activity. The ethylene normally charged may comprise gaseous constituents generally encountered in readily available ethylene, such as, for example, minor amounts of normally gaseous hydrocarbons other than ethylene. The oxygen may be employed in the form of relatively pure oxygen or as an oxygen-containing, normally gaseous material providing molecular oxygen for the reaction, such as, for example, air. Normally gaseous material, such as, for example, nitrogen, oxides of carbon, etc., as well as water, may be comprised in varying amounts in the carge to the oxidation.

The composition of the feed in the oxidation process can vary widely. Generally the volume ratio of oxygen to ethylene is in the range of about 100:1 to about 1:6, preferably about 20:1 to about 1:4. The flow rate of feed is generally in the range of about 2 to about 200 volumes of feed per volume of catalyst per hour.

A further understanding of the present invention will be provided by referring to the following examples:

EXAMPLE I

This example is a control and demonstrates the catalytic activity of a precipitated grade silver oxide on the oxidation of ethylene to ethylene oxide. For demonstration purposes, it was not considered necessary to perform the actual addition of alkali metal hydroxide to aqueous silver nitrate solution since this is normally the method used to prepare commercial silver oxide. In addition, barium oxide is added as a promoter. This is a known promoter used in this type reaction and is described in U.S. Pat. No. 2,831,870.

To 35 grams of a 10–20 mesh size alpha-alumina (Alcoa T-61, Aluminum Company of America) was added 11 grams of silver oxide, C. P. (Mallinckrodt, Inc.), 1.1 grams of barium oxide and 80 milliliters of distilled water. After thoroughly mixing all the ingredients, the bulk of the water was removed on a steam bath with stirring. The product was then dried in an air oven at 115° C. for about 16–20 hours to give a gray-black material. This material was then calcined (activated by heat) at 700° C. for 1 hour in a muffle furnace containing an atmosphere of air. A tan colored catalyst product was obtained.

A glass-lined 316 stainless steel reactor (0.5 in. × 14.5 in.) was employed which was equipped with a 3 millimeter I.D. glass thermowell, pressure gauge, gas inlet tube and gas mixer, gas outlet tube and septum for collecting samples. The reactor was externally wrapped with a heating tape. The bottom of the glass liner was comprised of either small holes or was glass fritted to retain the catalyst within the liner but still allow passage of gaseous products and reactants. The liner was charged with 5 milliliters (9.5 grams) of the catalyst described and the reactor sealed. The reactor was slowly heated to 200° C., temperature taken 2.5 inches from reactor bottom, while air was passed through at a rate of 189 milliliters/minute at STP. Ethylene was then passed through the reactor at a rate of 11 milliliters/minute at STP. The total gas volume was thus 200 milliliters/minute at STP. This is equivalent to a gas hourly space velocity (GHSV) of 2,400 with a catalyst contact time of 1.5 seconds. A sample was removed and analyzed on a 6 foot long gas chromatographic column. This column is referred to as a concentric tube reactor (CTR) available from Alltech Associates and is comprised of an inner column ($\frac{1}{8}$ inch O.D. diameter) packed with Porapak P (a crosslinked polystyrene) and an outer column ($\frac{1}{4}$ inch O.D. diameter) packed with 13X mol sieve. The CTR column was operated at 25° C. for 6 minutes and then heated to 225° C. at a rate of 8° C./minute using a helium gas flow of 60 milliliters per minute.

The run was repeated at several higher temperatures. The results of these runs are shown in Table I.

TABLE I

| Oxidation of Ethylene to Ethylene Oxide Using Silver Oxide (30 php[a] Ag) on Alumina Catalyst | | |
|---|---|---|
| Reaction Temperature, °C. | % Ethylene Conversion[b] | % Selectivity[b] Ethylene Oxide |
| 200 | 29 | 33 |
| 225 | 48 | 28 |
| 250 | 77 (60) | 30 (26) |
| 275 | 85 | 24 |
| 300 | 88 | 10 |
| 325 | 90 | 5 |

[a]Parts by weight of silver per hundred parts by weight of alumina support.
[b]Values in parenthesis are from repeat runs.

Optimum conditions appear to be about 225°–250° C. where the ethylene conversion is high with a high selectively to ethylene oxide. Above 250° C. ethylene oxide selectivity decreases significantly. Below 225° C. the ethylene conversion also decreases significantly.

EXAMPLE II

This example is an inventive run illustrating that silver nitrate can be deposited directly on an alumina support for subsequent use in the oxidation of ethylene to ethylene oxide without having to be first converted to silver oxide in a separate and isolated step.

To 20 grams of 10–20 mesh alpha-alumina (Alcoa T-61) was added 9.36 grams of silver nitrate dissolved in 4 milliliters of water. After thoroughly mixing, the mixture was dried in an air-containing oven at 115° C. for 16–20 hours followed by calcination in the presence of air at 700° C. for 1 hour.

The procedure for oxidizing ethylene to ethylene oxide described in Example I was repeated except 5 milliliters (9.0 grams) of the catalyst prepared according to Example II was employed. Various reaction temperatures were used. These results are listed in Table II.

TABLE II

| Oxidation of Ethylene to Ethylene Oxide Using Silver Nitrate (30 php[a] Ag) on Alumina Catalyst | | |
|---|---|---|
| Reaction Temperature, °C. | % Ethylene Conversion[b] | % Selectivity[b] Ethylene Oxide |
| 250 | 2.0 | trace |
| 300 | 26 (8) | 23 (20) |
| 325 | 33 (17) | 37 (24) |
| 350 | 43 (29) | 39 (44) |
| 375 | 59 | 40 |
| 400 | 74 | 4 |

[a]Parts of weight of silver per hundred parts by weight of alumina support.
[b]Values in parenthesis represent duplicate runs.

Optimum conditions appear to be about 350°–375° C., which is about 125° C. higher than the control in Example I. Nevertheless, for a given conversion level in the range of about 30 to about 60% the selectivity for the catalyst of Example II is greater than that for Example I. This equates to a higher overall yield of ethylene oxide with the catalyst of Example II than with the catalyst of Example I.

EXAMPLE III

This example is an invention run illustrating that when silver nitrate is deposited directly on a different type support than alumina similar advantages are produced. The support used in this example was magnesium oxide.

To 20 grams of commercial grade magnesium oxide (Norton Company) comprised of $MgO/SiO_2/CaO$ in a parts by weight ratio of 98/1/1 was added 9.36 grams of silver nitrate dissolved in 4 milliliters of water. After thoroughly mixing, the mixture was dried in an air-containing oven at 115° C. for 16–20 hours followed by calcination at 700° C. for 1 hour.

The procedure for oxidizing ethylene to ethylene oxide described in Example I was repeated except 5 milliliters (9.2 grams) of the catalyst prepared according to Example III was employed. Various reaction temperatures were used. These results are listed in Table III.

TABLE III

Oxidation of Ethylene to Ethylene Oxide Using Silver Nitrate (30 php[a] Ag) on Magnesium Oxide Catalyst

| Reaction Temperature, °C. | % Ethylene Conversion[b] | % Selectivity[b] Ethylene Oxide |
|---|---|---|
| 250 | 2 | c |
| 275 | 20 (10) | 77 (c) |
| 300 | 50 (32) | 50 (59) |
| 325 | 45 | 60 |
| 350 | 80 | 13 |

[a]Parts by weight of silver per hundred parts by weight of magnesium oxide support.
[b]Values in parenthesis represent duplicate runs.
[c]Due to the small amounts of ethylene feed employed reliable selectivity values were not obtained for conversions of less than about 20%.

Optimum conditions appear to be about 300°–325° C., which is about 50°–75° C. higher than the control in Example I. Nevertheless, here again for a given conversion level in the range of about 30 to about 60%, the inventive catalyst produced a higher overall yield of ethylene oxide than did the control.

Although certain preferred embodiments of the invention have been disclosed for the purpose of illustration it will be evident that various changes and modifications may be made therein without departing from the scope and spirit of the invention.

What is claimed is:

1. A process for preparing a catalyst for the oxidation of ethylene to ethylene oxide consisting essentially of combining aqueous silver nitrate with a suitable solid support in an amount which will result in said catalyst containing about 2 to about 75 weight percent silver based on the weight of said solid support, then drying the thus treated support at a temperature in the range of about 100° C. to about 200° C. to remove substantially all the water associated with said support, and then calcining the dried support at a temperature in the range of about 250° C. to about 800° C. to obtain an active catalyst.

2. A process according to claim 1 wherein said solid support is alpha-alumina.

3. A process according to claim 2 wherein said aqueous silver nitrate is employed in an amount which results in a catalyst containing about 10 to about 50 weight percent silver based on the weight of said solid support.

4. A process according to claim 3 wherein said alpha-alumina has a surface area of less than 1.0 $m^2/gm$.

5. A process according to claim 4 wherein said aqueous silver nitrate is employed in an amount which results in a catalyst containing about 30 weight percent silver based on the weight of said solid support and said calcining is conducted at a temperature in the range of about 500° C. to about 700° C.

6. A process according to claim 3 wherein said calcining is conducted at a temperature in the range of about 500° C. to about 700° C.

7. A process according to claim 1 wherein said solid support comprises magnesium oxide.

8. A process according to claim 7 wherein said aqueous silver nitrate is employed in an amount which results in a catalyst containing about 10 to about 50 weight percent silver based on the weight of said support.

9. A process for producing ethylene oxide comprising reacting ethylene and oxygen under suitable reaction conditions in the presence of a catalyst produced by a process consisting essentially of combining aqueous silver nitrate with a suitable porous solid support in an amount which will result in said catalyst containing 2 to 75 weight percent silver based on the weight of said solid support, then drying the thus treated support at a temperature no greater than about 200° C. to remove substantially all the water associated with said support, and then calcining the dried support at a temperature in the range of about 250° C. to about 800° C. until said catalyst is active for said oxidation process.

10. A process according to claim 9 wherein said ethylene and said oxygen are reacted at a temperature in the range of about 150° C. to about 500° C.

11. A process according to claim 10 wherein said solid support is alpha-alumina.

12. A process according to claim 11 wherein said catalyst contains about 10 to about 50 weight percent silver based on the weight of said alpha-alumina.

13. A process according to claim 12 wherein said alpha-alumina has a surface area of less than 1.0 $m^2/gm$.

14. A process according to claim 13 wherein said catalyst contains about 30 weight percent silver based on the weight of said alpha-alumina.

15. A process according to claim 10 wherein said solid support comprises magnesium oxide.

16. A process according to claim 15 wherein said catalyst contains about 10 to about 50 weight percent silver based on the weight of said solid support.

17. A process according to claim 16 wherein said catalyst was calcined at a temperature in the range of about 500° C. to about 700° C.

* * * * *